United States Patent
Cote, Sr. et al.

(10) Patent No.: US 7,837,658 B2
(45) Date of Patent: Nov. 23, 2010

(54) ANTI-DRAWBACK MEDICAL VALVE

(75) Inventors: Andrew L. Cote, Sr., Merrimack, NH (US); Brian L. Newton, Woonsocket, RI (US); Charles F. Ganem, Cape Neddick, ME (US)

(73) Assignee: Nypro Inc., Clinton, MA (US)

( * ) Notice: Subject to any disclaimer, the term of this patent is extended or adjusted under 35 U.S.C. 154(b) by 80 days.

(21) Appl. No.: 11/435,313

(22) Filed: May 16, 2006

(65) Prior Publication Data

US 2006/0293629 A1      Dec. 28, 2006

Related U.S. Application Data

(63) Continuation-in-part of application No. 11/058,381, filed on Feb. 15, 2005, and a continuation-in-part of application No. 10/291,448, filed on Nov. 7, 2002, now Pat. No. 6,869,426.

(60) Provisional application No. 60/681,275, filed on May 16, 2005, provisional application No. 60/645,644, filed on Jan. 21, 2005, provisional application No. 60/350,738, filed on Nov. 13, 2001.

(51) Int. Cl.
   *A61M 5/315*      (2006.01)
(52) U.S. Cl. .................... 604/236; 251/149.6
(58) Field of Classification Search .......... 604/249, 604/247, 251, 236; 251/149.2, 149.6, 149.1, 251/340
   See application file for complete search history.

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/112 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,352,531 A | 11/1967 | Kilmarx | 251/149.6 |
| 3,385,301 A | 5/1968 | Harautuneian | 128/349 |

(Continued)

FOREIGN PATENT DOCUMENTS

EP      0268480      5/1988

(Continued)

OTHER PUBLICATIONS

Heiko Krassow, *International Search Report and Written Opinion of the International Searching Authority*, May 10, 2006, 14 pages.

*Primary Examiner*—Kevin C Sirmons
*Assistant Examiner*—Deanna K Hall
(74) *Attorney, Agent, or Firm*—Sunstein Kann Murphy & Timbers LLP

(57) ABSTRACT

A medical valve includes a housing having an interior forming an inlet and an outlet. A longitudinally movable member is secured within the interior of the housing. External to the movable member and within the interior is a fluid path. Movement of the movable member controls fluid flow between the inlet and the outlet via the fluid path. The outlet produces no greater than a negligible drawback or positive push during withdrawal of a nozzle.

22 Claims, 10 Drawing Sheets

U.S. PATENT DOCUMENTS

| | | | |
|---|---|---|---|
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,819,908 A | 4/1989 | Norkey | 251/149.6 |
| 4,830,331 A * | 5/1989 | Vindum | 251/63 |
| 4,842,591 A | 6/1989 | Luther | 604/283 |
| 4,850,978 A | 7/1989 | Dudar et al. | 604/201 |
| 4,871,353 A | 10/1989 | Thomsen | 604/83 |
| 4,874,377 A | 10/1989 | Newgard et al. | 604/167 |
| 4,908,018 A | 3/1990 | Thomsen | 604/83 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A * | 4/1991 | Rogers et al. | 604/245 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,064,416 A | 11/1991 | Newgard et al. | 604/167 |
| 5,067,783 A | 11/1991 | Lampert | 385/60 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,163,922 A | 11/1992 | McElveen, Jr. et al. | 604/249 |
| 5,171,230 A | 12/1992 | Eland et al. | 604/250 |
| 5,190,067 A | 3/1993 | Paradis et al. | 137/1 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,338,002 A | 8/1994 | McNaughton et al. | 251/149.6 |
| 5,349,984 A | 9/1994 | Weinheimer et al. | 137/543.21 |
| 5,353,837 A | 10/1994 | Faust | 137/614.18 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,395,348 A | 3/1995 | Ryan | 604/247 |
| 5,401,255 A | 3/1995 | Sutherland et al. | 604/247 |
| 5,439,451 A | 8/1995 | Collinson et al. | 604/247 |
| 5,456,675 A | 10/1995 | Wolbring et al. | 604/280 |
| 5,458,640 A | 10/1995 | Gerrone | 604/264 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,665 A | 5/1996 | Fleetwood | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,535,771 A | 7/1996 | Purdy et al. | 137/15 |
| 5,535,785 A | 7/1996 | Werge et al. | 137/843 |
| 5,549,566 A | 8/1996 | Elias et al. | 604/167 |
| 5,555,908 A | 9/1996 | Edwards et al. | 137/329.1 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,618,268 A | 4/1997 | Raines et al. | 604/82 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,806,551 A | 9/1998 | Meloul et al. | 137/15 |
| 5,806,831 A | 9/1998 | Paradis | 251/149.1 |
| 5,820,601 A | 10/1998 | Mayer | 604/167 |
| 5,921,264 A | 7/1999 | Paradis | 137/15 |
| 5,967,490 A | 10/1999 | Pike | 251/149.1 |
| 6,029,946 A * | 2/2000 | Doyle | 251/149.1 |

| | | | |
|---|---|---|---|
| 6,036,171 A | 3/2000 | Weinheimer et al. ...... 251/149.1 |
| 6,039,302 A | 3/2000 | Cote, Sr. et al. .......... 251/149.1 |
| 6,048,335 A | 4/2000 | Mayer ......................... 604/167 |
| 6,050,978 A | 4/2000 | Orr et al. .................... 604/249 |
| 6,063,062 A | 5/2000 | Paradis ....................... 604/249 |
| 6,068,011 A | 5/2000 | Paradis ........................... 137/1 |
| 6,079,432 A | 6/2000 | Paradis ........................... 137/1 |
| 6,089,541 A | 7/2000 | Weinheimer et al. ...... 251/149.6 |
| 6,142,446 A | 11/2000 | Leinsing ................... 251/149.1 |
| 6,152,900 A | 11/2000 | Mayer ......................... 604/167 |
| 6,221,065 B1 | 4/2001 | Davis .......................... 604/539 |
| 6,228,069 B1 | 5/2001 | Barth et al. ................. 604/249 |
| 6,245,048 B1 | 6/2001 | Fangrow, Jr. et al. ........ 604/249 |
| 6,290,206 B1 | 9/2001 | Doyle ...................... 251/149.1 |
| 6,325,099 B1 | 12/2001 | Bunschoten et al. ... 137/614.04 |
| 6,344,033 B1 | 2/2002 | Jepson et al. ............... 604/256 |
| 6,428,520 B1 | 8/2002 | Lopez et al. ................. 604/249 |
| 6,482,188 B1 | 11/2002 | Rogers et al. ............... 604/249 |
| 6,543,745 B1 | 4/2003 | Enerson .................... 251/149.7 |
| 6,595,964 B2 | 7/2003 | Finley et al. ................ 604/246 |
| 6,609,696 B2 | 8/2003 | Enerson ......................... 251/86 |
| 6,669,673 B2 | 12/2003 | Lopez ........................ 604/249 |
| 6,745,998 B2 | 6/2004 | Doyle ...................... 251/149.6 |
| 6,755,391 B2 * | 6/2004 | Newton et al. ........... 251/149.6 |
| 6,871,838 B2 | 3/2005 | Raines et al. ............. 251/149.4 |
| 6,991,215 B2 | 1/2006 | Kiehne .................... 251/149.6 |
| 7,160,272 B1 | 1/2007 | Eyal et al. ................... 604/249 |
| 7,184,825 B2 | 2/2007 | Leinsing et al. ............... 604/20 |
| 2003/0050610 A1 | 3/2003 | Newton et al. .............. 604/256 |
| 2003/0093061 A1 | 5/2003 | Ganem ....................... 604/533 |
| 2003/0098430 A1 | 5/2003 | Leinsing et al. ......... 251/149.6 |
| 2003/0141477 A1 | 7/2003 | Miller ..................... 251/149.1 |
| 2004/0073171 A1 | 4/2004 | Rogers et al. .......... 604/164.13 |
| 2004/0124388 A1 | 7/2004 | Kiehne .................... 251/149.1 |
| 2005/0256460 A1 | 11/2005 | Rome et al. ................. 604/247 |
| 2006/0108555 A1 | 5/2006 | Kiehne .................... 251/149.7 |
| 2007/0218757 A1 | 9/2007 | Guala ......................... 439/589 |
| 2007/0246674 A1 | 10/2007 | Kiehne .................... 251/149.6 |
| 2008/0190485 A1 | 8/2008 | Guala ........................... 137/1 |

FOREIGN PATENT DOCUMENTS

| | | |
|---|---|---|
| EP | 0629418 | 12/1994 |
| EP | 0 791 371 B1 | 8/1997 |
| EP | 1243285 | 9/2002 |
| GB | 2079162 | 1/1982 |
| WO | WO 83/02559 | 8/1983 |
| WO | WO 93/11828 | 6/1993 |
| WO | WO 95/15193 | 6/1995 |
| WO | WO 96/00107 | 1/1996 |
| WO | WO 97/39791 | 10/1997 |
| WO | WO 98/22178 | 5/1998 |
| WO | WO 98/26835 | 6/1998 |
| WO | WO 98/39594 | 9/1998 |
| WO | WO 99/59672 | 11/1999 |
| WO | WO 00/44433 | 8/2000 |
| WO | WO 01/20218 | 3/2001 |
| WO | WO 03/018104 | 3/2003 |
| WO | WO 03/018105 | 3/2003 |
| WO | WO 2004/060466 | 7/2004 |

* cited by examiner

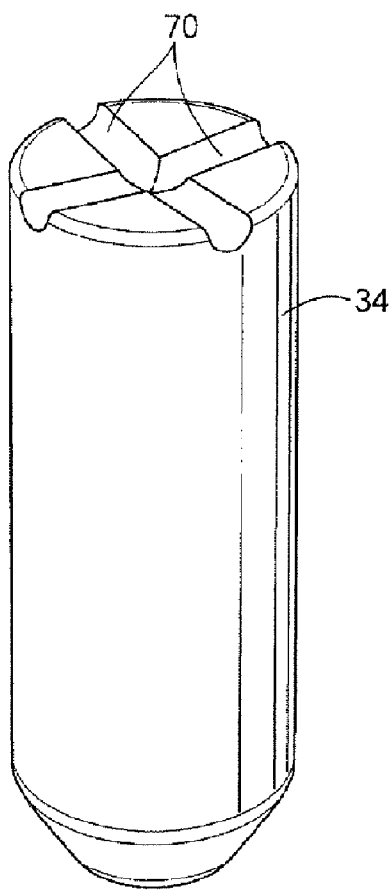 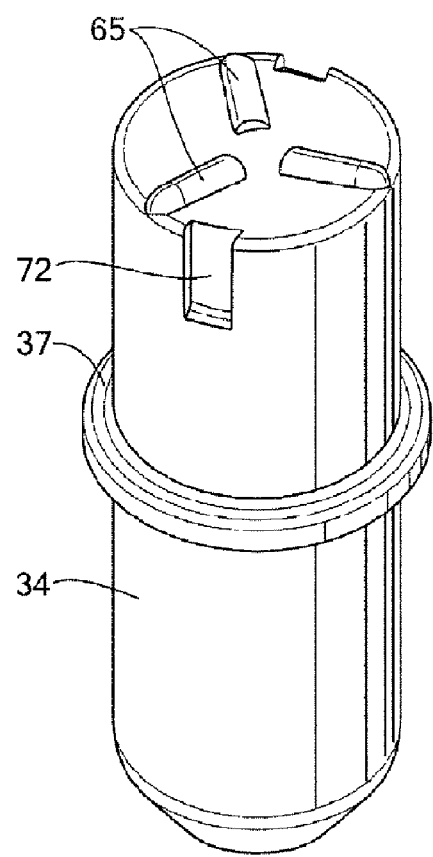
*FIG. 4*  *FIG. 5*

ANTI-DRAWBACK MEDICAL VALVE

CROSS REFERENCE TO RELATED APPLICATIONS

This application claims the benefit of U.S. patent application No. 60/681,275, filed May 16, 2005, entitled "Anti-drawback Medical Valve," the disclosure of which is incorporated herein by reference, in its entirety.

This application is also a continuation-in-part of U.S. patent application Ser. No. 11/058,381, filed Feb. 15, 2005, entitled "Anti-drawback Medical Valve," which in turn is a continuation-in-part of U.S. patent application Ser. No. 10/291,448, filed Nov. 7, 2002, issued as U.S. Pat. No. 6,869,426, entitled, "Anti-drawback Medical Valve," which in turn claims the benefit of provisional U.S. patent application No. 60/350,738, filed Nov. 13, 2001, entitled "Anti-drawback Medical Valve,". U.S. patent application Ser. No. 11/058,381 also claims priority from Provisional U.S. patent application No. 60/645,644, filed Jan. 21, 2005, entitled, "Anti-drawback Medical Valve,". Each of these patent applications described in this paragraph is hereby incorporated by reference, in its entirety.

TECHNICAL FIELD

The invention generally relates to medical valves and, more particularly, the invention relates to medical valves that substantially eliminate fluid drawback.

BACKGROUND ART

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a syringe into the proximal port of a properly secured medical valve to inject fluid into (or withdraw fluid from) a patient. Once inserted, the syringe may freely inject or withdraw fluid to and from the patient. Problems can arise, however, when the syringe is withdrawn. Specifically, a back pressure (i.e., a proximally directed pressure) produced by the withdrawing syringe undesirably can cause blood to be drawn proximally into a catheter attached to the valve, or into the valve itself. In addition to coagulating and impeding the mechanical operation of the valve, blood in the catheter or valve also compromises sterility.

SUMMARY OF THE INVENTION

In accordance with a first embodiment of the invention, a medical valve produces no greater than a negligible drawback or positive push during withdrawal of a nozzle. To those ends, the medical valve includes a housing having an interior forming an inlet and an outlet. A longitudinally movable member is secured within the interior of the housing. External to the movable member and within the interior housing is a fluid path. Movement of the movable member controls fluid flow between the inlet and the outlet via the fluid path. As noted above, the outlet produces no greater than a negligible drawback or positive push during withdrawal of a nozzle.

In accordance with related embodiments of the invention, the movable member may be a solid. The outlet produces no greater than a negligible drawback or positive push during attachment of the nozzle. The valve may further include at least one seal between the housing and the movable member.

The movable member may have a first position that permits fluid flow from the inlet to the outlet via the fluid path, and a second position that prevents fluid flow from the inlet to the outlet via the fluid path. The movable member may have a substantially static shape transitioning between the first position and the second position. The fluid path may have a volume that is substantially the same in both the first position and the second position. The valve may further include a biasing member for biasing the movable member toward the towards the second position. The biasing member may be a spring. The biasing member includes an air vent, which may further include a hydrophobic filter. The movable member may have an end for contacting the nozzle which may include at least one of a groove and a protrusion. The end may be swabbable in the second position.

In accordance with another embodiment of the invention, a method of controlling fluid flow through a medical valve is provided. The medical valve includes a housing having an inlet and an outlet. A longitudinally movable member is secured within the interior of the housing. The method includes inserting a nozzle into the inlet to cause the movable member to transition to a first position. In the first position, fluid flow is permitted between the inlet and the outlet, the fluid flow between the inlet and the outlet being external to the movable member. Withdrawing the nozzle from the inlet causes the movable member to transition to a second position that prevents fluid flow between the inlet and the outlet. The withdrawing includes causing the outlet to produce no greater than a negligible drawback or positive push.

In accordance with related embodiments of the invention, inserting the nozzle may produce no greater than a negligible drawback or positive push. The movable member may have a substantially static shape transitioning between the first position and the second position. The valve may include a fluid path within the interior of the valve, the fluid path having a volume that is substantially the same in both the first position and the second position. The method may further include biasing the movable member in the second position and/or venting gas between the interior of the housing and exterior of the housing.

In accordance with another embodiment of the invention, a medical valve has an open mode that permits fluid flow, and a closed mode that prevents fluid flow. The medical valve includes a housing having an interior forming an inlet and an outlet. Within the interior between the inlet and the outlet is a fluid path. A translating means controls fluid flow between the inlet and the outlet via the fluid path, with the fluid path external to the translating means. The outlet produces no greater than a negligible drawback or positive push during withdrawal of a nozzle.

In accordance with related embodiments of the invention, the translating means may longitudinally move within the interior. The translating means may have a substantially static shape transitioning between the first mode and the second mode. The fluid path may have a volume that is substantially the same in both the first position and the second position. The outlet may produce no greater than a negligible drawback or positive push during attachment of the nozzle.

BRIEF DESCRIPTION OF THE DRAWINGS

The foregoing features of the invention will be more readily understood by reference to the following detailed description, taken with reference to the accompanying drawings, in which:

FIG. 4 schematically shows an isometric view of a movable member of the medical valve of FIG. 1, in accordance with an embodiment of the invention;

FIG. 5 schematically shows an isometric view of an alternative embodiment of a movable member, in accordance with an embodiment of the invention;

DETAILED DESCRIPTION OF SPECIFIC EMBODIMENTS

In illustrative embodiments, a medical valve substantially has neither a positive push nor a drawback during withdrawal and/or attachment of a nozzle. To those ends, such a valve illustratively may have a flow path that maintains a substantially static shape and thus, a substantially constant volume, during withdrawal or attachment of the nozzle. Details of illustrative embodiments are discussed below.

Figure 1:
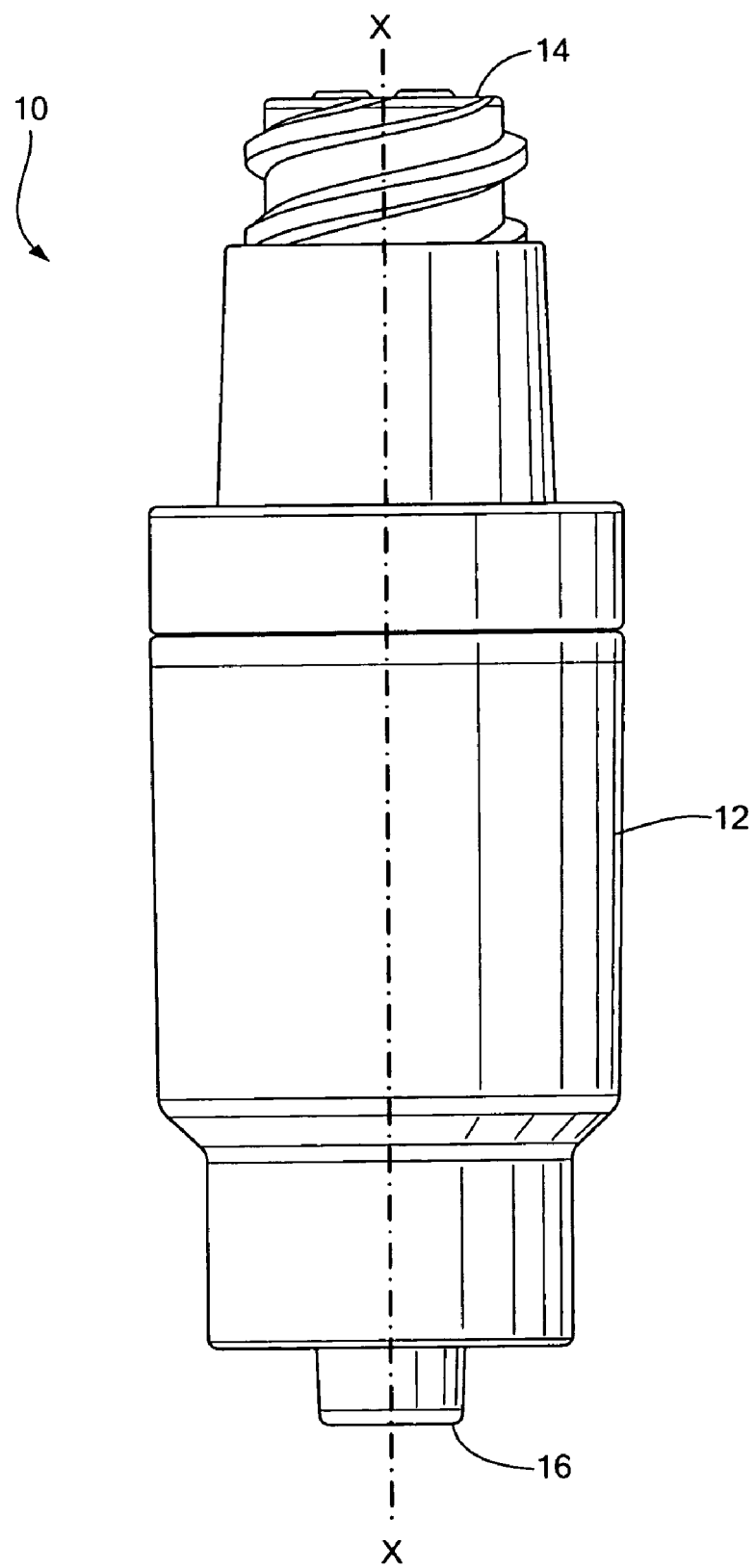
FIG. 1 schematically shows a medical valve that may be configured in accordance with illustrative embodiments.

FIG. 1 schematically shows a medical valve 10 that may be configured to substantially eliminate positive push and fluid drawback (a/k/a "back-flow") when a syringe or other type of nozzle is connected and/or withdrawn from it, in accordance with an embodiment of the invention. The valve 10 includes a proximal port 14 for receiving the nozzle, a valve body 12 having an internal valve mechanism (various embodiments of the valve mechanism are shown in subsequent figures) that controls fluid flow through the valve, and a distal port 16 for directing fluid between the valve 10 and a patient. The distal port may be at its location shown in FIG. 1, or at a different location, such as at a location orthogonal to the longitudinal dimension of the valve 10. Although much of the discussion herein refers to the proximal port 14 as a fluid inlet, and the distal port 16 as a fluid outlet, the proximal and distal ports 14 and 16 also may be respectively used as outlet and inlet ports.

Figure 2:
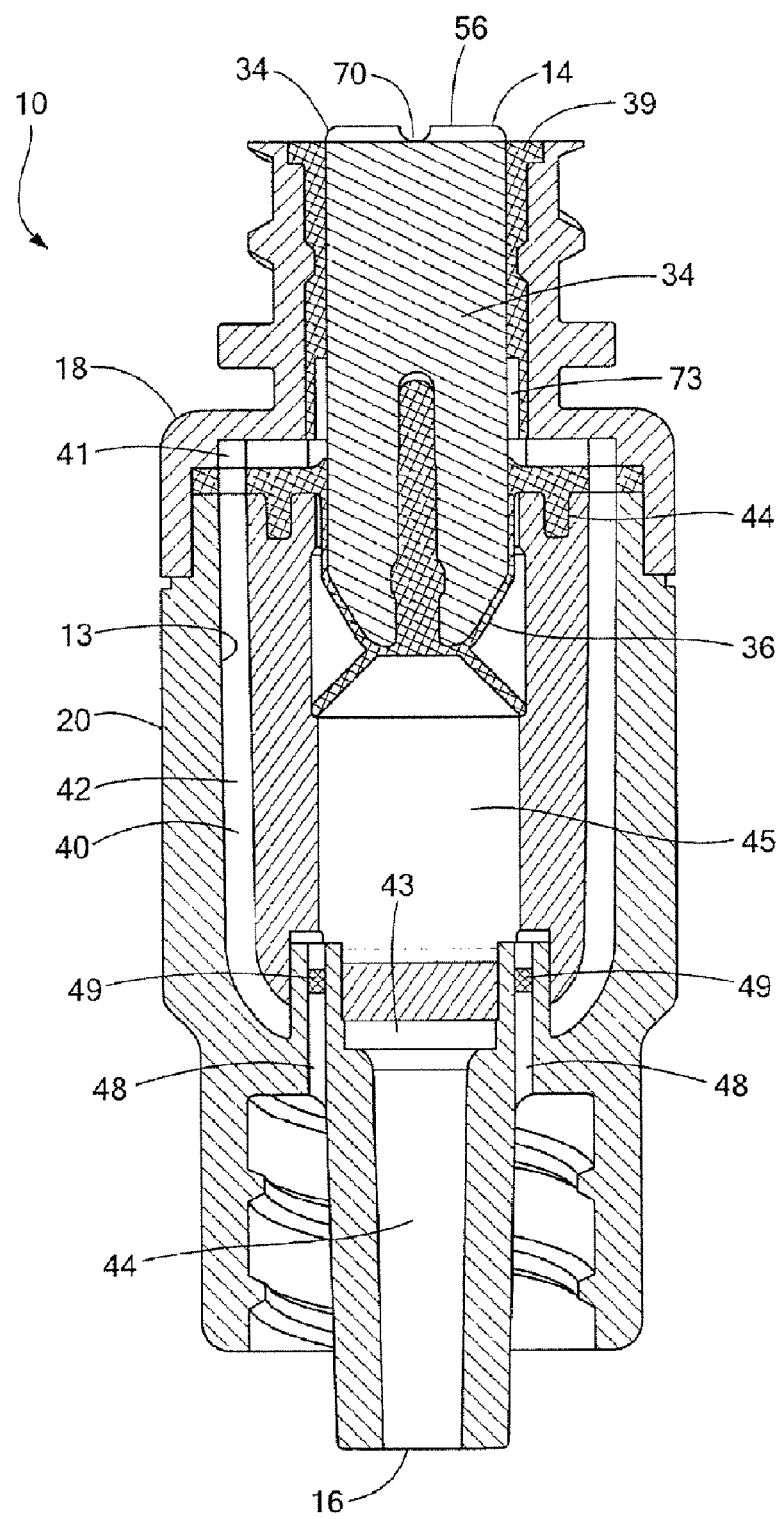
FIG. 2 schematically shows a cross-sectional view of the medical valve of FIG. 1 in a closed position, in accordance with an embodiment of the invention.
Figure 3:
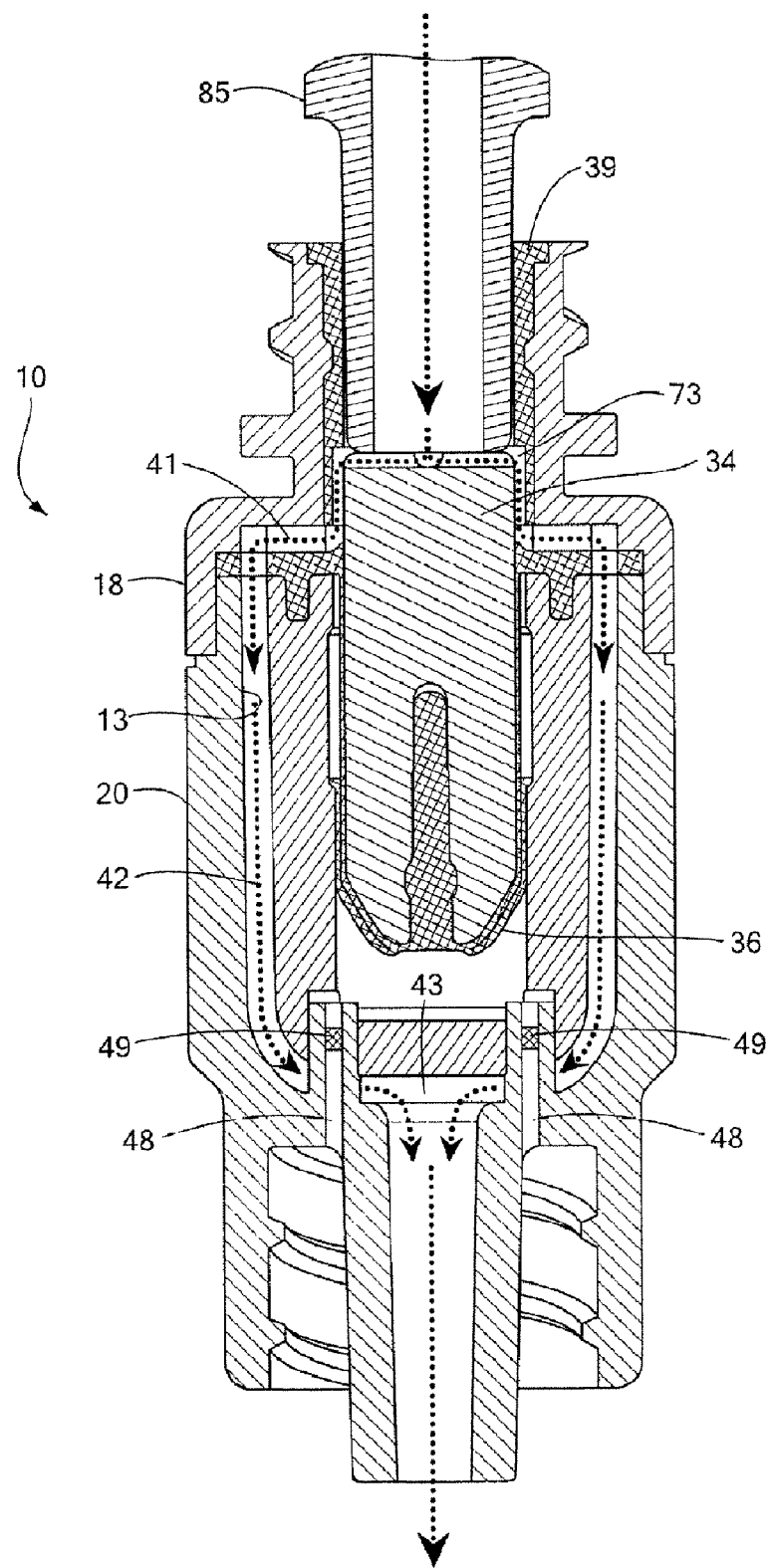
FIG. 3 schematically shows a cross-sectional view of the medical valve of FIG. 1 in an opened position, in accordance with an embodiment of the invention.

FIG. 2 schematically shows a cross-sectional view of one embodiment of the medical valve 10 (shown in FIG. 1 along line X-X) in a closed position, while FIG. 3 shows the valve 10 in an open position (e.g., activated by a luer-taper nozzle 85. The valve 10 includes a housing having an interior 13 forming the proximal and distal ports 14 and 16. The housing may be formed from inlet and outlet housing portions 18 and 20, which illustratively are formed from a hard plastic material (e.g., polycarbonate, polypropylene, or polyethylene) that are snap-fit together. For example, the housing portions 18 and 20 may be configured to snap fit together in accordance with the teachings of U.S. Pat. No. 6,892,998, the disclosure of which is incorporated herein, in its entirety, by reference. It should be noted that although some embodiments are discussed as being snap-fit components, various embodiments of the invention may be coupled by either snap-fit or other means, such as by an adhesive or ultrasonic welding. Accordingly, such embodiments are not intended to be limited to snap-fit components.

When coupled, the housing portions 18 and 20 form the interior 13, which is shaped to comply with the operation of its internal valve mechanism (discussed below) and permit fluid flow. The proximal port 14 illustratively is contoured to accept various types of nozzles, such as those complying with ANSI/ISO standards (e.g., luers complying with ANSI and/or ISO standards).

Secured within the interior 13 is a movable member 34 that may move, without limitation, substantially longitudinally to control fluid flow through the valve 10. The fluid, preferably in liquid form, such as blood, saline or a liquid medication, is controlled by the movable member 34 to pass through a fluid path within the interior 13 of the valve 10 between the inlet port 14 and the outlet port 16.

The movable member 34 is prevented from moving too far towards the distal port 16 by a spring 36 (described in more detail below). Furthermore, among other ways, the movable member 34 may be attached to the spring 36 by an interference fitting, welding and/or adhesive, such that the movable member 34 is prevented from moving too far towards the proximal port 14. In various embodiments, the movable member may include a flange 37 (see FIG. 5) that contacts the bottom edge of a luer insert 39 to prevent the movable member 34 from moving too far towards the proximal port 14.

FIG. 4 schematically shows an isometric view of the movable member 34, in accordance with an embodiment of the invention. In illustrative embodiments, the movable member 34 does not include a bore defining a portion of the fluid path. As a result, the fluid path is external to the movable member 34. The movable member 34 may be solid and/or rigid. The movable member 34 may have a substantially static shape when transitioning between the open and closed positions, and be made of, without limitation, a plastic or high durometer elastomeric material. Other materials may be used, however, so long as they can perform the functions discussed herein. The top end of the movable member may include at least one or more protrusions (e.g., ribs or bumps) and/or grooves 70. The grooves 70 or protrusions form passageways through which fluid can flow (discussed in more detail below).

Referring back to FIG. 2, when the valve 10 is in the closed position, the movable member 34 contacts the luer insert 39. The luer insert 39 acts as a seal and prevents fluid from entering or exiting the fluid path via inlet 14. The luer insert 39 may be attached to the inner wall of the housing by use of, without limitation, adhesives, a two-shot injection molding process, and/or an interference fitting (e.g., an undercut). Alternatively, the luer insert 39 may be attached to the movable member 34 such that it contacts the inner wall of the housing in the closed position to form a seal. The luer insert 39 may be made of, without limitation, a thermal set material (e.g., silicone) or a thermal plastic elastomer (e.g., kraton), and may be of the type described in U.S. Pat. No. 6,585,229, which is incorporated herein, in its entirety, by reference. In various embodiments, the luer insert 39 may be radially compressed when contacting the movable member 34.

The valve 10 also includes a flow path forming means 40 that forms the flow path through the valve and facilitates operations. Specifically, the flow path forming means 40 may include, without limitation, one or more elastomeric or plastic inserts, or may be integral to the housing (i.e., part of the housing). To facilitate fluid flow, the flow path means 40 may include, for example, a horizontal flow path 41 that leads to longitudinally extending flow paths 42. Such flow paths 42 further meet additional horizontal flow paths 43 that terminate in an outlet channel 44.

In addition to forming the flow path, the flow path forming means 40 may include attachment surfaces 44 that may work in combination with various surfaces of the valve housing to secure the spring 36. The spring 36, which may be made of, without limitation, silicone, contacts the distal end of the movable member 34 biases the movable member 34 such that the valve 10 is normally closed. In various embodiments, the spring 36 is neutral (i.e., neither compressed nor stretched) in the closed position. In other embodiments, the spring 36 is slightly stretched when the valve 10 is in the closed position.

Additionally, the flow path forming means 40 includes a central cavity 45 that permits longitudinal movement of the movable member 34. An air vent 48 may be connected to the central cavity to reduce pressure build up in the central cavity 47 due to longitudinal movement of the movable member 34. The air vent 48 may include a filter 49, such as sterilizing grade, hydrophobic vent filter that allows gas to flow through it but prevents any fluids and/or contaminants from entering the central cavity 45. The air vent 48 may allow gas to be expelled externally to the valve 10. Alternative embodiments, however, omit the air vent 48.

When the valve 10 is in the fully closed position, the top end of the movable member 34 may be flush with, or extend slightly above, the exterior inlet face of the housing. The top end 56 and the exterior inlet face thus present a swabbable surface. In other words, the top end 56 and the exterior inlet face may be easily wiped clean by any conventional means, such as with an alcohol swab. As mentioned in various ones of the noted incorporated documents, valves having swabbable surfaces are known in the art as "swabbable valves." In other embodiments, however, the valve 10 is not a swabbable valve.

Insertion of a nozzle 85 (e.g., a luer) into the proximal port 14 forces the movable member 34 to move longitudinally to an open position, as shown in FIG. 3. When in the open position, fluid may flow from the nozzle 85, through passageways formed by at least one or more protrusions (e.g., ribs or bumps) and/or grooves 70 in the top end of movable member 34 (typically the top end of the movable member 34 is primed with fluid before the movable member 34 reaches the open position). Fluid flowing through the passageways further flows into the flow path defined by flow path forming means 40, thereby permitting fluid flow between the inlet 14 and the outlet 16. It should be noted that during all phases of the opening and closing operations, the movable member 34 illustratively traverses through a portion of the fluid path. Consequently, substantially no volume changes occur in the fluid path.

Since there is substantially no volume change in the fluid path, both when the nozzle 85 is inserted into or withdrawn from the inlet 14, the valve 10 should generate no greater than a negligible positive or negative pressure through the outlet 16. In other words, in such embodiments, the volumes of fluid forced through the outlet 16 during withdrawal and insertion are negligible. This design, which has insubstantial positive push and/or drawback, thus may be considered to have a "neutral" drawback. In practice, this embodiment can have negligible amounts in either direction (e.g., less than one microliter). For example, if the nozzle is a tapered luer, the taper may result in a negligible volume change in the fluid path when in the open position, which should not occur with a taperless nozzle.

Figure 6:
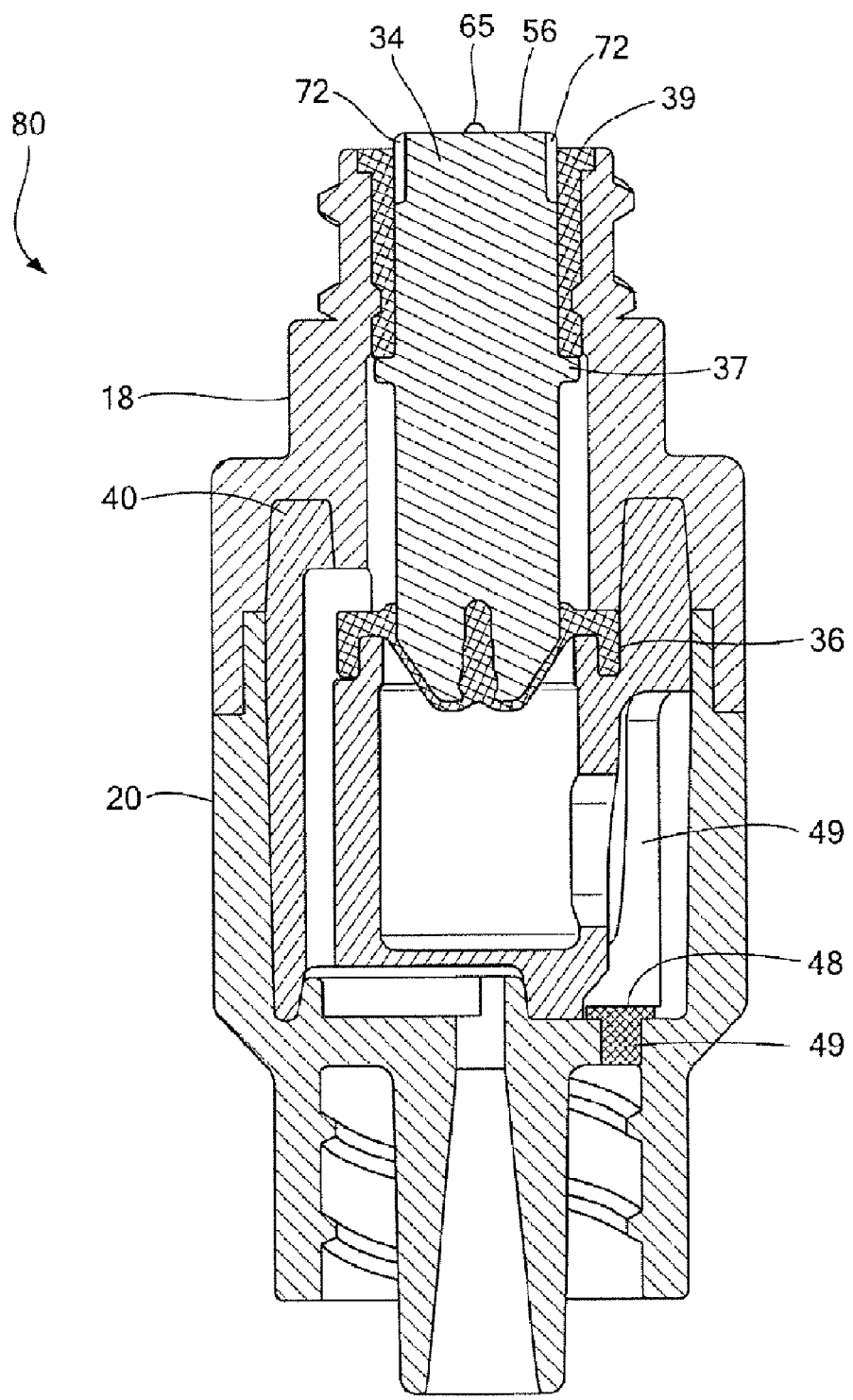
FIG. 6 schematically shows a cross-sectional view of a medical valve in a closed position, in accordance with an embodiment of the invention.
Figure 7:
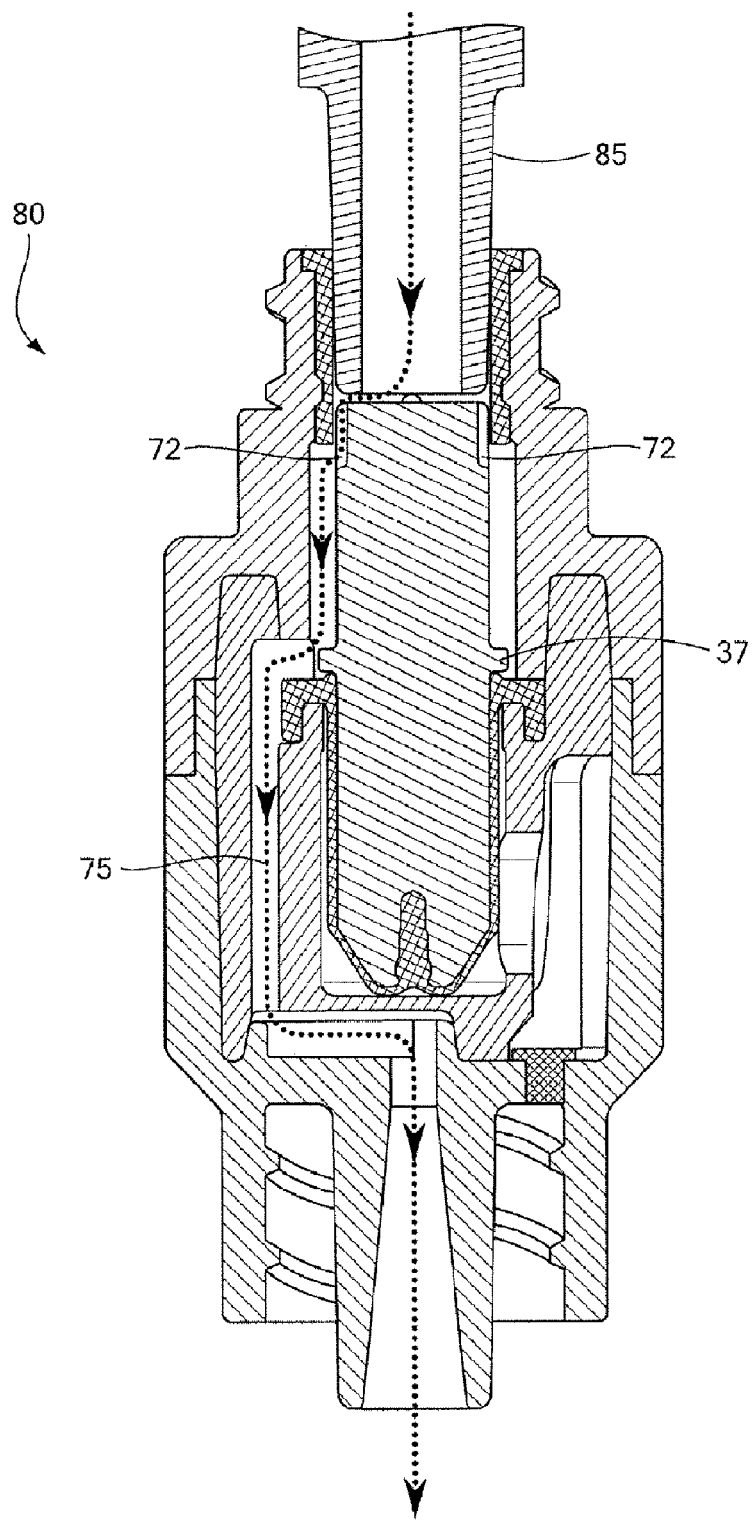
FIG. 7 schematically shows a cross-sectional view of the medical valve of FIG. 6 in an opened position, in accordance with an embodiment of the invention.
Figure 8:
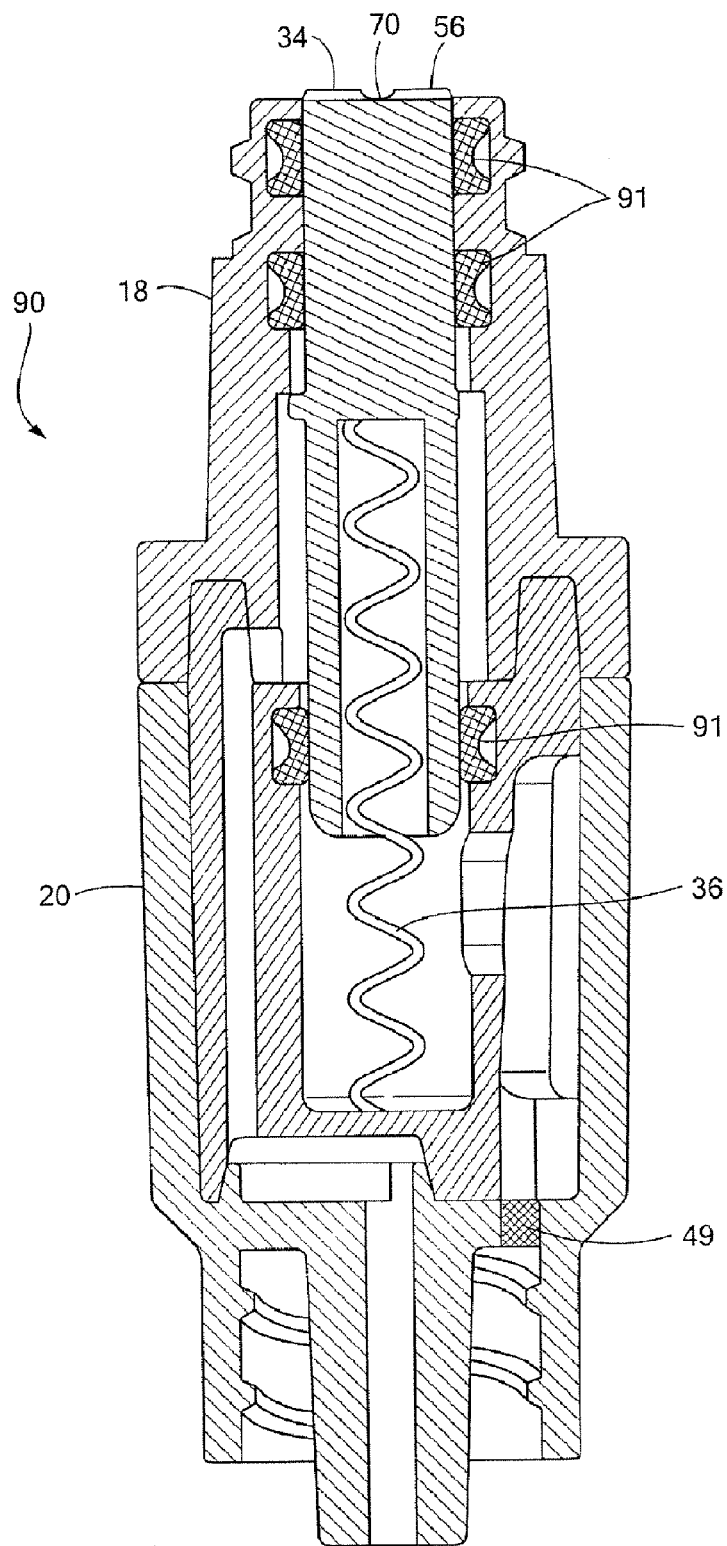
FIG. 8 schematically shows a cross-sectional view of a medical valve in a closed position, in accordance with an embodiment of the invention.
Figure 9:
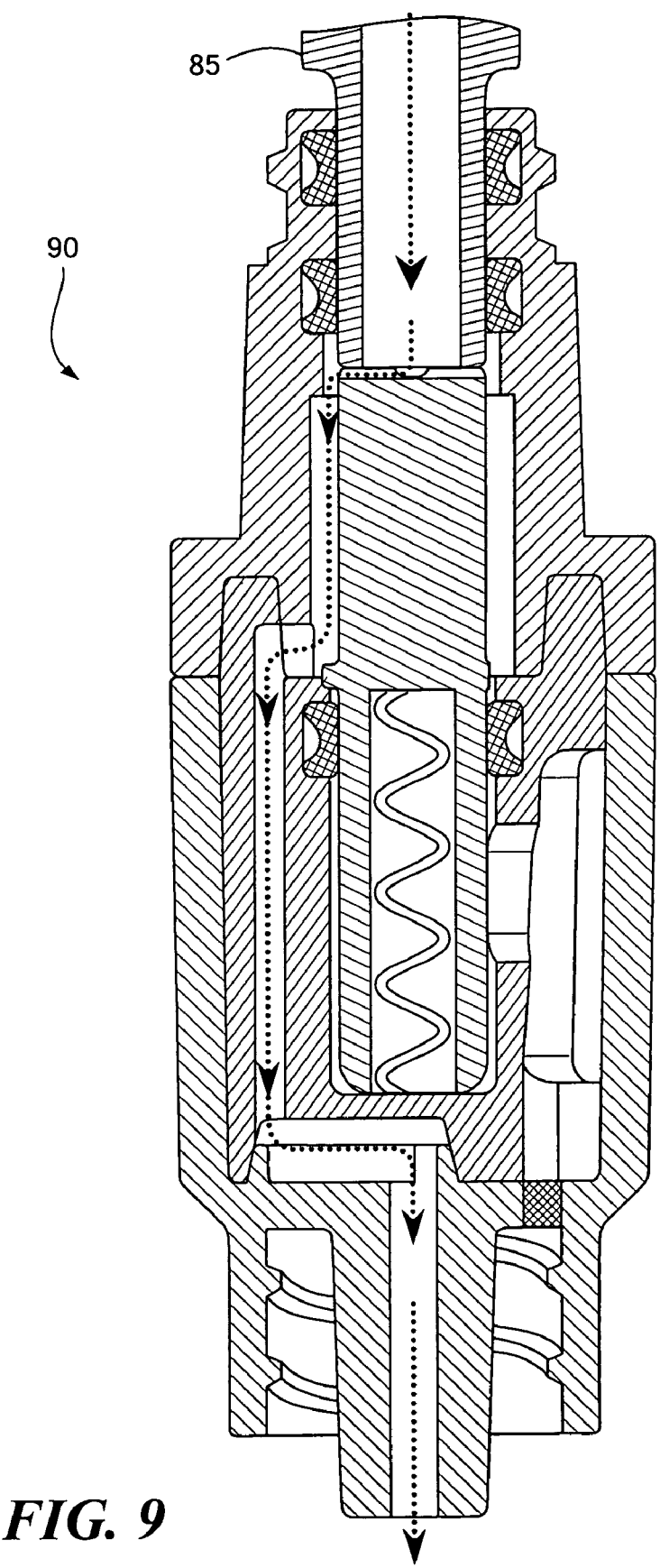
FIG. 9 schematically shows a cross-sectional view of the medical valve of FIG. 8 in an opened position, in accordance with an embodiment of the invention.

FIGS. 6 and 7 schematically show cross-sectional views of the medical valve 10 configured in a different manner than shown in FIGS. 2 and 3. Specifically, this embodiment incorporates a different embodiment of the movable member 34, which is depicted in FIG. 5. More specifically, instead of, or in addition to, at least one protrusion 65 and/or groove on the top of movable member 34, this embodiment of the movable member 34 has at least one groove 72 that extends downwardly from the top of the movable member 34. FIG. 6 shows the valve 80 in a non-activated/closed position, while FIG. 7 shows the valve 80 in an open/actuated position by a luer-taper nozzle 85. The valve 80 works in a similar manner to the valve 10 depicted in FIGS. 2 and 3, with exceptions, for example, of fluid flow associated with the nozzle 85 and movable member 34, the use of a flange 37 to secure the movable member 34 within the housing, and an additional cavity 49 to further reduce pressure build up in the central cavity 47.

More particularly, upon insertion, the tip of the nozzle 85 makes contact with the movable member 34. As the movable member 34 moves longitudinally towards the distal port 16, the grooves 72 extend past the luer insert 39. Fluid from the nozzle 85 passes through the gap between the protrusions 65, and further through the grooves 72 into the fluid path forming means 40, thereby permitting fluid flow between the inlet 14 and the outlet 16, as depicted by the dotted line 75 in FIG. 7.

In various embodiments, grooves 73 may be positioned on the luer insert 39 (see FIG. 3). The grooves 73 may extend upwardly from the bottom end of the luer insert 39 a predefined distance. Upon insertion of the nozzle 85, the movable member 34 moves longitudinally towards the distal port 16, such that fluid passing through passageways formed by the protrusions and/or grooves 70 on the top of the movable member 34 can flow into the grooves 73 on the luer insert 39 and into the fluid path.

Figure 10:
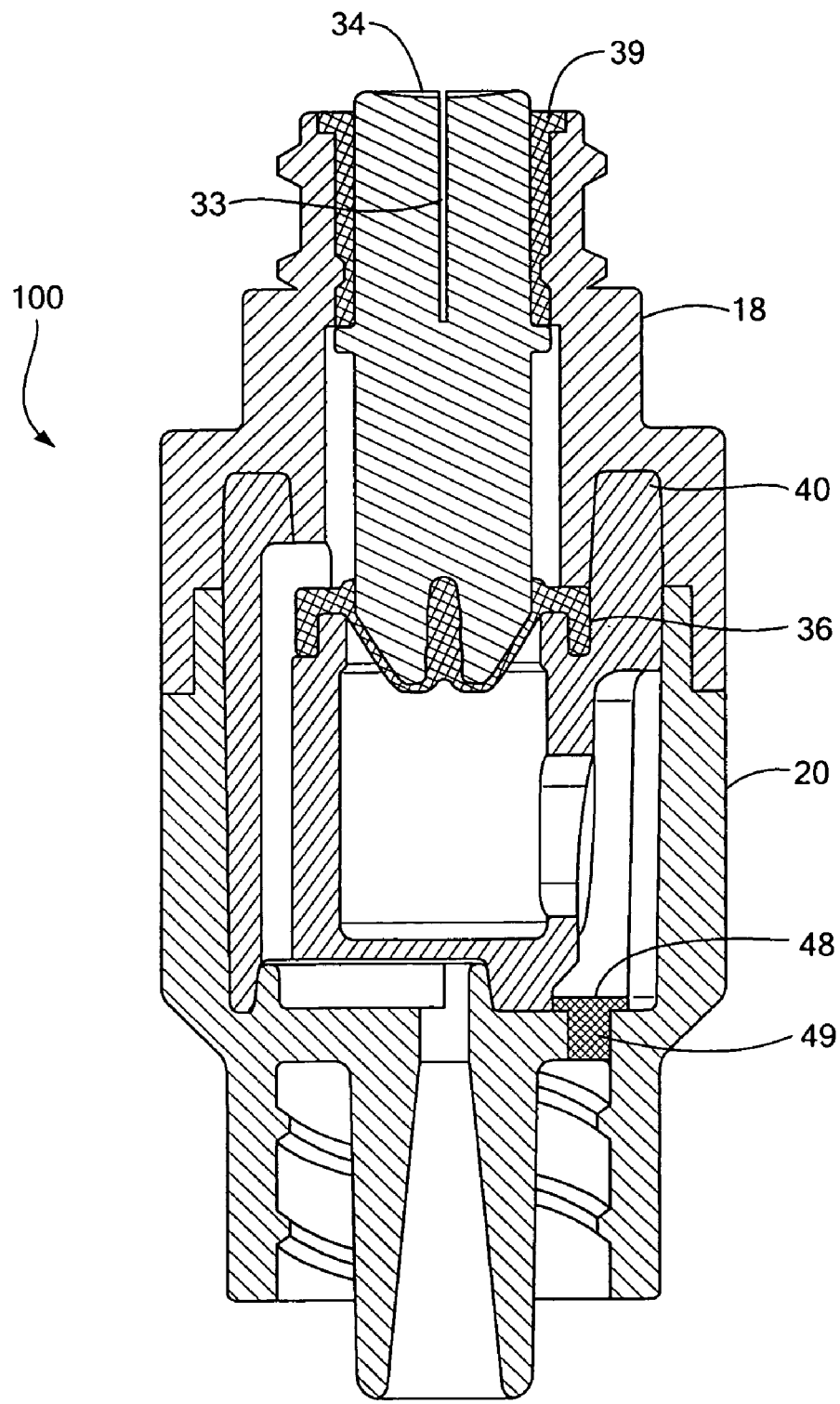
FIG. 10 schematically shows a cross-sectional view of a medical valve in a closed position, in accordance with an embodiment of the invention.
Figure 11:
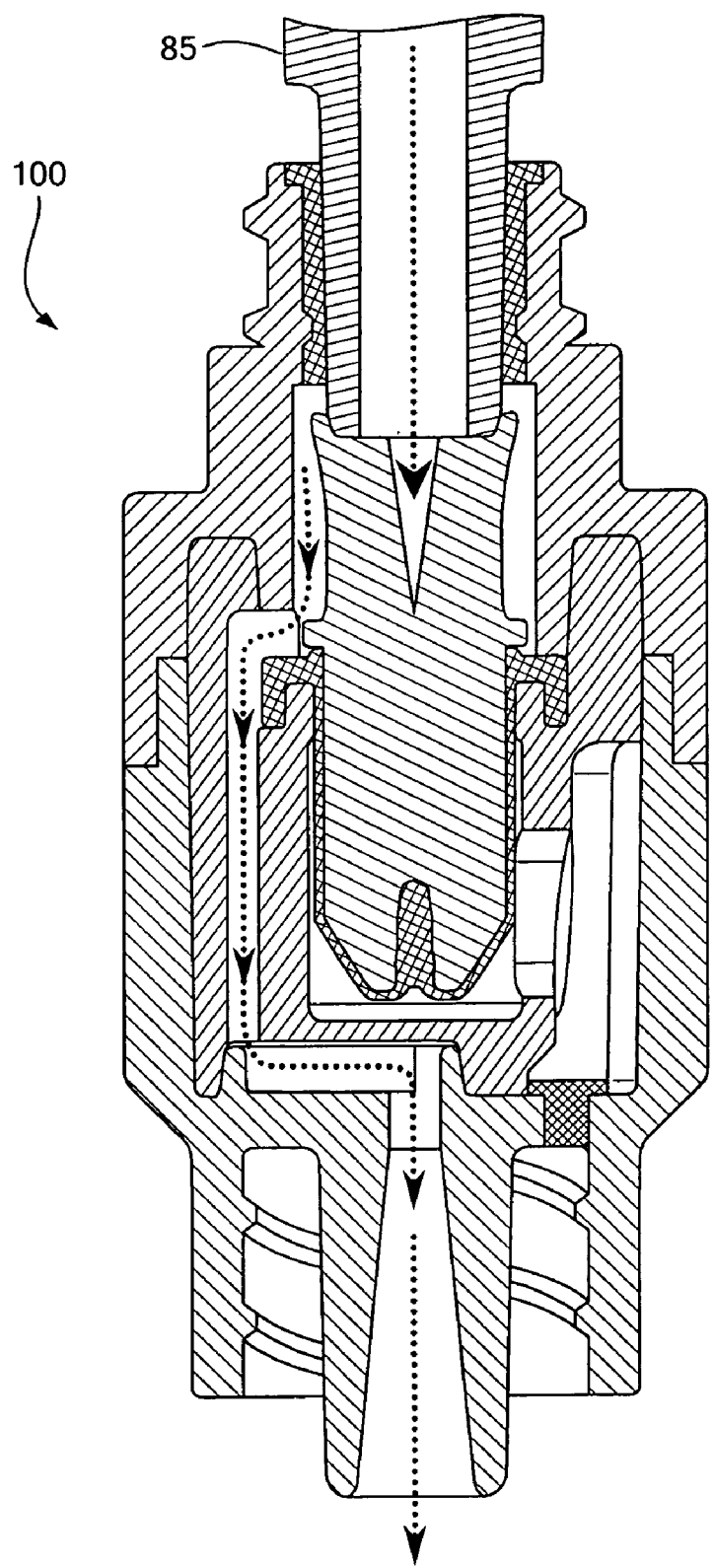
FIG. 11 schematically shows a cross-sectional view of the medical valve of FIG. 10 in an opened position, in accordance with an embodiment of the invention.

FIGS. 10 and 11 schematically show cross-sectional views of still another embodiment of a medical valve. FIG. 10 shows the valve 100 in a non-activated closed position, while FIG. 11 shows the valve 100 in an open position actuated by a luer-taper nozzle 85. Instead of protrusions or grooves on the top of the movable member 34, the top end of the movable member includes a split 33 that extends longitudinally from its proximal end (i.e., the end closest to the proximal port 14). In preferred embodiments, the slit 33 is dimensioned such that it does not extend distally beyond the luer insert 39 when the valve 10 is in the closed position. When the valve 10 is in the closed position, the post 34 contacts the luer insert 39, and the slit 33 is closed, thus preventing fluid from entering and/or exiting slit 33. In preferred embodiments, the post 34 may be radially compressed when adjacent the luer insert 39.

Insertion of a nozzle 85 (e.g., a luer) into the proximal port 14 forces the post 34 to move (radially and longitudinally) to an open position. The proximal end of the post 34 may be concave, such that the slit 33 opens when the nozzle presses against the post 34 and moves past the luer insert 39. When in that position, fluid may flow from the luer insert 39 through the slit 33 and further into the flow path forming means 40 thereby permitting fluid flow between the inlet 14 and the outlet 16, as depicted by the dotted line in FIG. 11.

Although the above discussion discloses various exemplary embodiments of the invention, it should be apparent that those skilled in the art can make various modifications that will achieve some of the advantages of the invention without departing from the true scope of the invention. For example, those skilled in the art can selectively combine features of the above-described embodiments to form a valve having the desired functionality.

What is claimed is:

1. A medical valve comprising:
a housing having an interior forming an inlet and an outlet;
a fluid path within the interior; and
a longitudinally movable member secured within the interior of the housing, the fluid path being external to the movable member, movement of the movable member controlling fluid flow between the inlet and the outlet via the fluid path,
the movable member having a first position that permits fluid flow from the inlet to the outlet via the fluid path, and a second position that prevents fluid flow from the inlet to the outlet via the fluid path, the fluid path having a volume that is substantially the same in both the first position and the second position,
the outlet producing no greater than a negligible drawback during withdrawal of a nozzle, the outlet also producing no greater than a negligible positive push during withdrawal of the nozzle.

2. The medical valve according to claim 1, wherein the movable member is solid.

3. The medical valve according to claim 1, wherein the movable member has a first position that permits fluid flow from the inlet to the outlet via the fluid path, and a second position that prevents fluid flow from the inlet to the outlet via the fluid path, the movable member having a substantially static shape transitioning between the first position and the second position.

4. The medical valve according to claim 1, wherein the outlet produces no greater than a negligible drawback or positive push during attachment of the nozzle.

5. The medical valve according to claim 1, wherein the valve has a first position that permits fluid flow from the inlet to the outlet via the fluid path, and a second position that prevents fluid flow from the inlet to the outlet via the fluid path, the valve further including a biasing member for biasing the movable member toward the second position.

6. The medical valve according to claim 5, wherein the biasing member is a spring.

7. The medical valve according to claim 6, wherein the biasing member includes an air vent.

8. The medical valve according to claim 7, wherein the air vent includes a hydrophobic filter.

9. The medical valve according to claim 1, wherein the movable member has an end for contacting the nozzle, the end including at least one of a groove and a protrusion.

10. The medical valve according to claim 1, further comprising at least one seal between the housing and the movable member.

11. The medical valve according to claim 1, wherein the movable member has a first position that permits fluid flow from the inlet to the outlet via the fluid path, and a second position that prevents fluid flow from the inlet to the outlet via the fluid path, the movable member having an end for contacting the nozzle, the end being swabbable in the second position.

12. A method of controlling fluid flow through a medical valve, the medical valve including a housing having an inlet and an outlet, the medical valve further including a longitudinally movable member secured within the interior of the housing, the method comprising:
inserting a nozzle into the inlet to cause the movable member to transition to a first position that permits fluid flow between the inlet and the outlet, wherein fluid flow between the inlet and the outlet is external to the movable member; and
withdrawing the nozzle from the inlet to cause the movable member to transition to a second position that prevents fluid flow between the inlet and the outlet, the withdrawing comprising causing the outlet to produce no greater than a negligible drawback, the withdrawing also comprising causing the outlet to produce no greater than a negligible positive push, the valve including a fluid path within the interior of the valve, the fluid path having a volume that is substantially the same in both the first position and second position.

13. The method according to claim 12, wherein inserting the nozzle produces no greater than a negligible drawback or positive push.

14. The method according to claim 12, wherein the movable member has a substantially static shape transitioning between the first position and the second position.

15. The method according to claim 12, further comprising biasing the movable member in the second position.

16. The method according to claim 15, further comprising venting gas between the interior of the housing and exterior of the housing.

17. A medical valve having an open mode that permits fluid flow, and a closed mode that prevents fluid flow, the medical valve comprising:
a housing having an interior forming an inlet and an outlet;
a fluid path within the interior, the fluid path having a volume that is substantially the same in both the open mode and the closed mode; and
translating means for controlling fluid flow between the inlet and the outlet via the fluid path, the fluid path external to the translating means;
the outlet producing no greater than a negligible drawback during withdrawal of a nozzle, the outlet also producing no greater than a negligible positive push during withdrawal of the nozzle.

18. The medical valve according to claim 17, wherein the translating means longitudinally moves within the interior.

19. The medical valve according to claim 17, wherein the translating means has a substantially static shape transitioning between the open mode and the closed mode.

20. The medical valve according to claim 17, wherein the outlet produces no greater than a negligible drawback or positive push during attachment of the nozzle.

21. The medical valve according to claim 1, wherein the inlet and outlet are longitudinally aligned.

22. The method according to claim 12, wherein the inlet and outlet are longitudinally aligned.

* * * * *